United States Patent
Requejo et al.

(10) Patent No.: US 7,410,513 B2
(45) Date of Patent: Aug. 12, 2008

(54) CLEAN-BURNING FRAGRANCE CANDLE WITH CONSISTENT FLAME SIZE AND BURN RATE

(75) Inventors: Luz P. Requejo, Racine, WI (US); Kim C. Materna, Waukesha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 295 days.

(21) Appl. No.: 10/291,160

(22) Filed: Nov. 8, 2002

(65) Prior Publication Data

US 2004/0088906 A1    May 13, 2004

(51) Int. Cl.
   *C11C 5/00*    (2006.01)
(52) U.S. Cl. ............................................. 44/275
(58) Field of Classification Search ............ 44/275; 431/288
   See application file for complete search history.

(56) References Cited

U.S. PATENT DOCUMENTS

| 802,100 A | 10/1905 | Gray |
|---|---|---|
| 809,121 A | 1/1906 | Lewy |
| 1,462,601 A | 7/1923 | Hohmann |
| 1,866,025 A | 7/1932 | Geller |
| 1,950,813 A | 3/1934 | Pungs et al. |
| 1,950,814 A | 3/1934 | Pungs et al. |
| 3,797,990 A | 3/1974 | Rogers et al. |
| 3,843,312 A | 10/1974 | Easterday |
| 4,110,261 A | 8/1978 | Newland |
| 4,515,909 A | 5/1985 | Sawano et al. |
| 4,568,270 A | 2/1986 | Marcus |
| 4,714,496 A * | 12/1987 | Luken et al. ............... 106/270 |
| 5,010,685 A | 4/1991 | Sakamoto et al. |
| 5,854,284 A | 12/1998 | Abraham |
| 6,079,975 A | 6/2000 | Conover |
| 6,159,254 A | 12/2000 | Akiyama et al. |
| 6,165,234 A | 12/2000 | Kanakkanatt |
| 6,544,303 B2 * | 4/2003 | Calzada ....................... 44/275 |

FOREIGN PATENT DOCUMENTS

| DE | 124 191 | | 2/1977 |
|---|---|---|---|
| DE | 212530 | * | 8/1984 |
| EP | 0 685 554 | | 6/1995 |
| JP | 07-48591 | | 2/1995 |

* cited by examiner

*Primary Examiner*—Cephia D Toomer

(57) ABSTRACT

A wax composition comprising a high molecular weight aliphatic alcohol, a low molecular weight ethylene vinyl acetate copolymer, at least one odorant, and a wax. The odorant is substantially retained in the wax composition when the wax composition is exposed to temperatures below a melting point of the wax composition. Furthermore, the odorant is emitted from the wax composition when the wax composition is exposed to temperatures at or above the melting point of the wax composition.

24 Claims, 3 Drawing Sheets

EXAMPLES OF WAX COMPOSITIONS WITH VARYING LEVELS OF EVA, HMWA, AND MICROWAX.

| FORMULA | FRAGRANCE | MICROWAX CONTENT (PERCENT) | EVA CONTENT (PERCENT) | $C_{18}$-$C_{22}$ ALCOHOL CONTENT (PERCENT) | BURN TIME (HOURS) | RETENTION (GRAMS) | CARBON DEPOSIT (1-5 SCALE) | COKING (0-5 SCALE) |
|---|---|---|---|---|---|---|---|---|
| CONTROL 1 | COUNTRY GARDEN | 5 | 0 | 0 | 26.33 | 6.52 | 1.23 | 1.73 |
| 1 | COUNTRY GARDEN | 0 | 2.5 | 0 | 28.3 | 3.21 | 1.2 | 1.5 |
| 2 | COUNTRY GARDEN | 0 | 0 | 5 | 32.55 | 5.64 | 1.2 | 0.0 |
| 3 | COUNTRY GARDEN | 0 | 0 | 12 | 36.87 | 8.4 | 0.2 | 0.0 |
| 4 | COUNTRY GARDEN | 0 | 1 | 5 (EUROPEAN) | 32.85 | 3.66 | 0.2 | 0.0 |
| 5 | COUNTRY GARDEN | 0 | 1 | 5 (DOMESTIC) | 38.62 | 3.74 | 0.7 | 0.0 |
| 6 | COUNTRY GARDEN | 0 | 2 | 3 | 29.95 | 3.92 | 0.9 | 0.8 |
| 7 | COUNTRY GARDEN | 0 | 1 | 3 | 27.93 | 3.25 | 0.7 | 1.8 |
| CONTROL 2 | VANILLA | 5 | 0 | 0 | 31.22 | 32.24 | 0.2 | 0.4 |
| 8 | VANILLA | 0 | 1 | 5 | 36.10 | 46.25 | 0.0 | 0.0 |

FIG. 2

EXAMPLES OF WAX COMPOSITIONS WITH VARYING PARAFFINS.

| FORMULA | FRAGRANCE AND PARAFFIN SUBSTITUTIONS | MICROWAX CONTENT (PERCENT) | (EVA) CONTENT (PERCENT) | $C_{18}$-$C_{22}$ ALCOHOL CONTENT (PERCENT) | BURN TIME (HOURS) | RETENTION (GRAMS) | CARBON DEPOSIT (1-5 SCALE) | COKING (0-5 SCALE) |
|---|---|---|---|---|---|---|---|---|
| CONTROL 3 | STRAWBERRIES AND CREAM | 5 | 0 | 0 | 28.62 | 7.45 | 1.0 | 1.5 |
| 9 | STRAWBERRIES AND CREAM + IGI WAX | 0 | 1 | 5 | 30.02 | 8.75 | 0.5 | 0.0 |
| 10 | STRAWBERRIES AND CREAM + ASTOR WAX | 0 | 1 | 5 | 31.47 | 7.94 | 0.5 | 0.0 |
| CONTROL 4 | LAVENDER MEADOWS | 5 | 0 | 0 | 28.49 | 13.08 | 0.00 | 0.00 |
| 11 | LAVENDER MEADOWS + IGI WAX | 0 | 1 | 5 | 30.63 | 23.92 | 0.00 | 0.00 |
| 12 | LAVENDER MEADOWS + ASTOR WAX | 0 | 1 | 5 | 36.86 | 15.16 | 0.00 | 0.00 |

FIG. 3

CLEAN-BURNING FRAGRANCE CANDLE WITH CONSISTENT FLAME SIZE AND BURN RATE

BACKGROUND OF THE INVENTION

1. Field of the Invention

This invention relates to clean-burning fragrance candles with a consistent flame size and burn rate. Furthermore, this invention relates to wax compositions used in the candles, methods of manufacturing the candles, and the manufacture of the wax compositions used in the candles.

2. Description of Related Art

Fragrance-emitting candles are widely available and are typically employed to impart odorant into a space. Generally, the odorant will mask other odors, or simply impart its own, in order to make a space more pleasant.

Early fragranced candles included mixtures of wax, odorant, and optional additives, such as colorant. Such candles were generally manufactured by cooling a molten wax composition, typically containing paraffin, around a candle wick. The solidified wax composition, at a microscopic level, includes wax crystals packed against each other. Components of a wax composition, such as colorant, are typically trapped in the inter-crystal spaces. Fragrance molecules, however, are typically too small to be held in these inter-crystal spaces. Consequently, in early fragrance candles, the fragrance molecules often diffused through the candle while the candle was in solid form. This diffusion eventually brought the fragrance molecules to the surface, leading to weeping, even when the candle was lit. In addition to the loss of fragrance, weeping gave a wet, greasy, feel to the candles.

The problem of weeping was eventually brought under control by the addition of chemicals that reduce the crystal size in the solidified candle wax. The smaller crystals pack tightly enough to trap the odorant inside their inter-crystal spaces.

Typically, microwax or large olefinic materials are mixed with the main wax composition to keep the crystal size, and the inter-crystal spaces, smaller. Generally, microwax is the product remaining after vacuum distillation of crude oil products at high temperatures and reduced pressure to isolate a target product. The target product is usually paraffin wax, the main wax content of candles. Such leftover products forming the microwax may include larger paraffins. Olefinic materials, in the form of alkanes, may be obtained from a variety of sources, such as the petroleum industry, and typical sizes for these alkenes includes those with ten or more carbon atoms.

While the use of microwax and olefinic materials (referred to collectively as "microwax" herein) is beneficial in reducing fragrance loss in candle waxes, there are negative affects imparted to candles employing these compounds, including, for instance, (i) higher processing temperatures, (ii) coking, (iii) carbon deposits, and (iv) inconsistent flame sizes and burn rates.

The processing temperatures are generally higher because microwax has higher melting temperatures than the main wax utilized in candle compositions (typically paraffin wax of smaller sizes than microwax).

Coking and carbon deposits left by candles employing microwax result from incomplete combustion of the microwax used. These materials often do not burn completely because they are very large and tend to only partially oxidize, thereby yielding smoke and coking the candle surface.

The flame size and burn rates among different candles, and even for an individual candle over its life, employing microwax may be inconsistent. There are two main reasons for these inconsistencies. First, the source of the microwax or olefinic product may vary from batch to batch, because the inconsistent composition of crude oil product yields varying microwax or olefinic compositions. This variability may cause otherwise similar candles to burn differently. Second, these materials often do not completely mix with the balance of the candle wax composition, yeilding areas with different concentrations of these compounds. This non-homogeneity causes flame size and burn rate to vary, even with respect to an individual candle over time.

Ethylene vinyl acetates ("EVAs") have been used as a partial substitute for microwax in fragranced candles, to lessen the problems associated with these materials. U.S. Pat. No. 4,110,261 discusses the use of EVAs, in general, in candle wax compositions. This patent is hereby incorporated by reference in its entirety. EVAs are known to make the crystal size smaller as well as assisting in making such candles release from manufacturing molds easier. EVAs also are known to make candles more opaque. However, because EVAs may cause similar smoking and coking, undesirable characteristics are still present in such candles employing EVAs as a partial substitute for or addative to the microwax. In addition, we have found that, when EVAs are used as a complete substitute for microwax, smoking and residues may become higher than in the case of olefinic or microwax-containing candles.

High molecular weight alcohols ("HMWAs") are known to make candle flames more luminous and white. The use of these alcohols has been partially disclosed in U.S. Pat. No. 1,950,814, which is hereby incorporated by reference in its entirety. However, HMWAs have not been used a substitute for microwax inasmuch as they alone do not impart the ability to retain fragrance within the wax.

We have found that a combination of such alcohols with EVAs may be used as a substitute for microwax in fragranced candle waxes, and that substitution of the combination results in candles with qualities superior to those of candles using microwax or olefinic materials. For example, such candles typically exhibit less smoke and coking, while producing a more consistent flame size and burn rate, all without the problem of weeping.

BRIEF SUMMARY OF THE INVENTION

It is an object of our invention to provide a fragranced wax composition, for use in candles, that does not weep fragrance, burns with a consistent flame size and burn rate, exhibits reduced coking and smoking, and may be processed at lower temperatures, particularly compared to candles utilizing substantial amounts of microwaxes or olefinic materials.

It is a second object of our invention to provide methods of manufacturing such wax compositions and candles using them.

In a first embodiment, our invention is directed to a wax composition comprising a high molecular weight aliphatic alcohol, a low molecular weight ethylene vinyl acetate copolymer, at least one odorant, and a wax. The odorant is substantially retained in the wax composition when the wax composition is exposed to temperatures below a melting point of the wax composition. Furthermore, the odorant is emitted from the wax composition when the wax composition is exposed to temperatures at or above the melting point of the wax composition.

In one aspect of the first embodiment, the low molecular weight ethylene vinyl acetate is in an amount of about 0.5 percent to about 8 percent, by weight, of the wax composition. In a second aspect of the first embodiment, the high molecular weight alcohol is in an amount of about 1 percent to about 20 percent, by weight, of the wax composition. In a third aspect of the first embodiment, the wax component of the composition is a paraffin wax. In a fourth aspect of the first embodiment, the odorant is in an amount of about 0.5 percent to about 30 percent, by weight.

In a second embodiment, our invention is directed to a method of making a candle. The method comprises the following steps: (1) heating a wax to its melting point; (2) mixing (i) a high molecular weight alcohol, (ii) a low molecular weight ethylene vinyl acetate, and (iii) at least one odorant with the wax to form a wax composition; and (3) casting the wax composition in a mold. The odorant is substantially retained in the wax composition when the wax composition is exposed to temperatures below a melting point of the wax composition, and is emitted from the wax composition when the wax composition is exposed to temperatures at or above the melting point of the wax composition.

In other preferred embodiments, the wax composition may further comprise additional materials such as colorants, ultraviolet inhibitors, and oxidation inhibitors.

BRIEF DESCRIPTION OF THE DRAWINGS

FIG. 2 is a table of experimental results showing our invention to have qualities superior to conventional wax compositions.

FIG. 3 is a table of experimental results showing our invention to have qualities superior to conventional wax compositions.

DETAILED DESCRIPTION OF THE INVENTION

Figure 1:
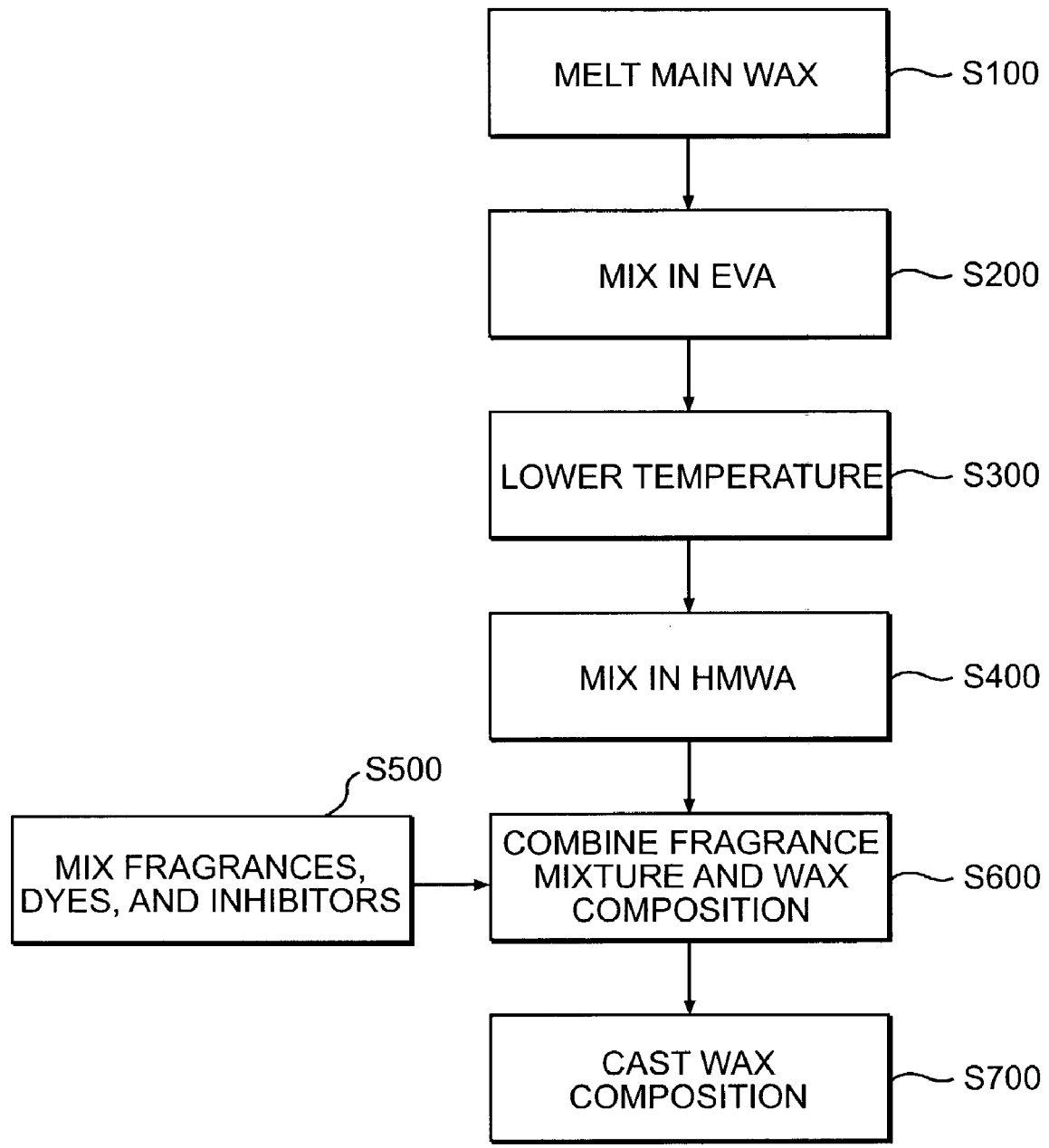
FIG. 1 is a flowchart of a method of making candles according to our invention.

We have found that combining a high molecular weight alcohol and a low molecular weight ethylene vinyl acetate copolymer in a wax composition provides for a superior fragranced candle, as compared to candles employing microwax or olefinic materials.

A preferred candle of the current invention comprises a wax composition having about 0.5 percent to about 8 percent, by weight of the composition, low molecular weight ethylene vinyl acetate, about 1 percent to about 20 percent, by weight of the composition, high molecular weight alcohol, about 0.5 percent to about 30 percent, by weight of the composition, odorant, and the balance may be made of a typical candle wax, such as paraffin wax, as well as other materials.

Other components of the wax composition may include colorants in an amount of about 0.00001 percent to about 3 percent, by weight, UV inhibitors in an amount of about 0.1 to about 5 percent, by weight, and oxidation inhibitors in an amount of about 0.1 percent to about 5 percent, by weight.

High Molecular Weight Alcohol

Preferably, the high molecular weight alcohol ("HMWA") used in the wax composition is typically a linear-chain aliphatic alcohol, wherein the alcohol moiety is placed terminally. These HMWAs are preferably comprised of about 18 to about 22 carbon atoms, e.g., 1-octadecanol, 1-nonadecanol, 1-eicosanol, etc.

Although typically 18 to 22 carbons atoms in size, the alchols used may be made larger or smaller, depending on the preferences of the manufacturer. In choosing an alcohol, the artisan should note that when using larger HMWAs, smaller amounts are usually needed. When using smaller HMWAs, coking and soot may become a problem. As such, adjustments may be needed when mixing the components of the wax composition of the invention.

The preferred amount of alcohol to be used in our compositions ranges between about 1 to about 20 percent, by weight, of the total composition. Most preferably, between about 5 and about 20 percent is used.

HMWAs may be obtained from industry-standard resources. For example, Oil Associates, Inc., of Cleveland, Ohio manufactures alcohols of preferred characteristics. Alcohols obtained from manufacturers typically come in solid or liquid form. Little preparation is needed for the incorporation into a composition of our invention. Typically, for solids, the manufacturer would melt the alcohol and pour the alcohol into the wax composition in the proper proportion. Such preparations are well known.

Low Molecular Weight Ethylene Vinyl Acetate

Low molecular weight ethylene vinyl acetate ("EVA") copolymers are those copolymers formed from ethylene and vinyl acetate monomers. EVAs, in combination with the HMWAs, impart the ability of a candle to hold the fragrance molecules while reducing smoke and coking.

The preferred EVAs are those with molecular weights of about 5000 molecular weight units, or less. A more preferred range for these molecular weights is from about 1000 to about 3000 molecular weight units. We have found these molecular weight ranges useful because higher molecular weight copolymers may flow into candle wicks too slowly, making them difficult to burn. Also, larger weight copolymers may not completely combust, leading to coking.

Ethylene vinyl acetates ("EVAs"), in combination with HMWAs, help to provide clean and consistent flame sizes and burn rates, the reduction of coking and soot, and lower processing temperatures.

Preferably, EVAs are provided in an amount of about 0.5 percent to about 8 percent, by weight, of the final composition. Higher amounts may lead to smoking and coking, while lower amounts may not be enough to retain the fragrance within the candle wax composition. EVA co-polymers are known in the industry and may be obtained from standard manufacturers. A few preferred EVAs include ElvaX™ 200, available through the Dupont de Nemours Company of Wilmington, Del., as well as OK 5415 and ASTORLITE™ CH, both of which are available through the Honeywell-Astor Company of Morristown, N.J.

EVAs are typically purchased as a solid in the form of flakes, beads, or prill. To incorporate an EVA into a candle wax composition, the manufacturer simply needs to heat it to its melting temperature, and mix it with the other ingredients.

Main Wax

To form a candle, the EVAs and HMWAs are mixed with a main wax product that gives the candle its wax properties. Even in conventional candles, such a main wax is used, although it would be supplemented with microwax instead of a mixture of EVAs and HMWAs. For the main wax, typically paraffin wax is used.

The term "paraffin wax," as used here, describes a mixture of products derived from the vacuum distillation of crude petroleum products. Paraffin wax has the general formula $C_nH_{2n+2}$. The value of n may vary widely, but typically is between about 18 and about 30. The melting temperature of the wax varies directly with the value of n. A value of n of about 18 to about 30 generally yields preferred melting temperatures for a candle. Preferred melting temperatures are between about 120° F. and about 160° F. for free-standing candles, and between about 120° F. and about 127° F. for container candles. Paraffin waxes with such melting temperatures allow for candles that are slow burning and, when used in container candles, do not harm their containers.

Paraffins of different sizes may be used, with the ratio of the respective concentrations being varied to yield other desirable properties, such as bending and blocking resistances. Such options are described in U.S. Pat. No. 6,159,254, which is hereby incorporated herein in its entirety.

Straight-chain paraffins are preferred in our invention over branched-chain paraffins. Straight-chain paraffins tend to be less sticky, and have better burn and wicking properties. Typically, the smaller paraffins contain a higher percentage of straight-chain paraffins. Preferred paraffins are those paraffins that contain 85% or more straight-chain paraffins. Most preffered paraffins are those paraffins that contain 90% or more straight-chain paraffins.

Paraffin waxes, because of their petroleum source, typically contain oils in their composition. It is preferable to limit the amount of oil content in the paraffin when manufacturing waxes for container candles. These oils typically raise the burn temperature of the wax, creating a potential danger to the container. Preferred waxes for container candles are those with less than about 5% oil content.

Paraffin waxes are often used due to their cost-effective nature; however, other waxes may be substituted. For example, vegetable and animal waxes may be used. Two preferred waxes, other than paraffin, include soy and coconut waxes. In addition, mixing and substitutions are possible because, although having a different chemical structure, these waxes have similar properties with regard to crystal formation in the solid. Therefore, artisans may easily adjust the amounts of the various wax components.

Various main wax compositions for use in candles may be obtained from manufacturers including the Honeywell-Astor Company of Morristown, N.J., the Petrolite Corporation of Tulsa, Okla., and the Shell Corporation of Houston, Tex.

The incorporation of the wax into the total composition simply requires mixing the same at a temperature that will melt the wax. A manufacturer may prefer to melt the wax before all other components, as it is generally the largest single component of the wax compositions of our invention. In doing this, the manufacturer gains a larger volume of molten product in which to melt other components.

Odorants

Odorants are chemicals that impart a fragrance to a space. Any one of many types of odorants may be employed, depending on the manufacturer's preferences. Normally, the amount of odorant is determined experimentally, as is known in the art. In such experiments, the odorant may be increased to a point where the amount of odorant released is enough to impart the amount of scent desired, at or below peak fragrance strength. Use of more than the amount at peak fragrance strength will not impart any additional advantage. Disadvantages of using higher amounts of fragrance include the possibility of conferring a mottled appearance to the candle, weeping, and poor burn properties. Preferred amounts of odorant typically comprise from about 0.5 percent to about 30 percent, by weight, of the wax composition. More preferred amounts of odorant are in an amount of about 3 percent to about 12 percent, by weight.

Some typical odorants may include scents with floral, fruity, spicy, woody, aldehydic, and citrus scents. Odorants may be used singly, or in combination, to provide different levels of complexity. Combinations of odorants may also be used to obtain different qualities. The manufacturer, with the assistance of a fragrance company, may easily obtain a combination and amount of odorant to suit its needs.

Odorants are available through arts and crafts suppliers, as well as flavor and fragrance manufacturers, such as the International Flavor and Fragrance Company of Hazlet, N.J. and Takasago International Corporation of Rockleigh, N.J.

Odorants are generally oily substances that may be incorporated into the wax compositions of our invention by first dissolving any pigments, ultraviolet inhibitors, and oxidation inhibitors into the fragrance. That mixture is then added to the melted wax composition, which, after mixing, may be incorporated in the manufacturer's articles, i.e., candles.

Colorants

Generally, colorants are incorporated to provide for a visually appealing candle.

The choice and mixture of colorants is typically open to the needs of the manufacturer. Color mixing guides are available in the industry, and may be used to assist in the choice of colorants. Generally, the colorants used may be divided into two catagories, dyes and pigments.

Dyes are typically made of organic molecules and may be subject to photobleaching and oxidation. Preferred dyes include those that are oil soluble, and hence may be dissolved in a fragrance employed in the practice of our invention. Dyes that are not soluble in oil may cause the wick to clog and/or impart poor burning characteristics and non-uniform coloration of candles.

Pigments are typically inorganic minerals and are often insoluble in oil. They may, however, provide color to the candle by being suspended in the wax. Pigments typically offer the advantage of not being subject to degradation by photobleaching. Care is typically taken to avoid pigments with particle sizes that are too large, and consequently cause candle wick clogging.

Generally, it is preferred to avoid the use of pigments in container candles. In container candles, the insoluble pigment is not allowed to drip off the candle, and instead may pool about the wick, causing the wick to clog.

In some cases, the use of both dyes and pigments is preferred. For instance, a dye may be used in the body of the candle, and after formation of the candle, an overlayer is cast onto the candle using a pigment-containing wax. This combination offers coloration throughout the candle, while protecting the exposed surface of the candle from color fading.

Dye and pigment manufacturers, such as BASF of Germany or Clairiant Corporation of Switzerland, would be able to assist in choosing dyes and/or pigments of use to the manufacturer.

As mentioned earlier, dyes may be mixed with the fragrance and then mixed into the molten wax composition. Pigments are typically insoluble in oil and therefore are generally mixed into the wax composition and then dispersed by agitation while the wax composition solidifies.

Ultraviolet ("UV") Inhibitors and Oxidation Inhibitors

UV inhibitors are chemical compounds that protect the components of the candle wax from degrading to exposure to ultraviolet light. Oxidation inhibitors, similar to the UV inhibitors, generally protect the components of the wax from oxidative degration, which is typically exacerbated by heat. As such, each of these optional components of the wax composition has similar guidelines for choice of types and amounts. Therefore, in our discussion below, when we refer to "inhibitors," we collectively mean UV inhibitors and oxidation inhibitors.

Generally, the dyes and fragrances used within these wax compositions are susceptible to such UV and oxidative degradation. Typically, when the dyes degrade, the wax becomes dull and fades in color. Similarly, the degradation of fragrance may yield a candle with less scent, or even a scent that is undesirable.

A preferred amount of inhibitor would be an amount that is completely soluble in either the paraffin wax or the fragrance, ensuring uniform dispersion through the candle. However, it is also preferred to limit the inhibitor to a minimal amount that protects the component(s) of interest. The use of greater amounts of inhibitors would typically only increase the cost to manufacture the wax composition. The choice of amounts is left to design considerations, although both the UV inhibitors and oxidative inhibitors are preferably kept in an amount of about five percent, by weight, or less.

Inhibitors used in candle wax compositions are known in the industry. There are readily available guidelines to help the manufacturer choose a suitable inhibitor. Sometimes, it may be preferable to have multiple inhibitors in a wax composition. This may occur when the components that need to be protected require multiple types of UV and/or oxidative protection. Again, the manufacturer is referred to industry guidelines in choosing these inhibitors. Companies such as the BASF Corporation of Parsippany, N.J., which manufactures the preferred UVINUL™ series of UV inhibitors, may prove quite helpful in choosing a UV inhibitor to suit the manufacturer's needs. One example of a preferred UV inhibitor is UNIVIL™ 3008, manufactured by BASF Corporation of Mount Olive, N.J. For oxidation inhibitors, BASF and other manufacturers may similarly prove a valuable resource.

Method of Manufacture

Compositions according to our invention, and candles made therefrom, may be manufactured by any of a number of methods. A preferred method is set forth below, and shown in FIG. 1.

First, the wax is heated to about 180° F. or about 190° F., yielding a molten wax, to which the components may be added, in step 100 in FIG. 1. The wax is typically heated in large vats. After melting the wax, the low molecular weight EVA is typically added first, by hand, and the mixture is agitated until clear, indicating a uniformly mixed solution, in step 200.

After that, the temperature is typically lowered to about 165° F., and the HMWA is added, as shown in steps 300 and 400. Agitation of the solution is continued until the solution is again homogeneous.

In step 500, in a separate container, the fragrances, dyes, and inhibitors may be pre-mixed at room temperature, by hand. Those mixed components are then typically added, in step 600, to the vat of wax, EVA, and HMWA, and agitation is continued for another 10-20 minutes.

The mixture is poured into molds or containers with a prepositioned wick, in step 700, for container candles. Upon cooling, these candles are ready for use.

Alternatively, in the case of free-standing candles, the molten wax composition may be sprayed into granules or flakes. Such particulate material is then typically used as the basis for compression-molding of candles.

In compression-molding, the particulate material is typically added to a press that has prepositioned wicks. Such presses may be of a rotary type, which are capable of manufacturing a large numbers of candles, usually of smaller sizes, rapidly. Alternatively, a hydraulic press may be used. Typically, the hydraulic press is capable of much higher pressures and useful in the manufacture of larger candles, although the rate of manufacture is generally lower than in the case of rotary presses. The press compresses the wax particulate into solid candles about the prepositioned wicks. The candle may then be overdipped with a second wax, as mentioned above with respect to the colorants section. After cooling, the candles are ready for use.

Experimental Examples

Our experiments show that fragrance candles made with mixtures of low molecular weight EVA and HMWA provide a superior set of characteristics over candles formed with microwax, EVA alone, or HMWA alone. FIG. 2 shows a table of the results of a set of our experiments demonstrating the benefit of the present invention over the use of microwax, EVA alone, and HMWA alone.

For each formula set forth in the table in FIG. 2, fifteen container candles were manufactured, of which ten were tested, with the average test values being set forth in the table. The five candles left over were not examined and instead saved as retains for future reference. For Control 1, no EVA or HMWA was used. For each of formulas 1-7, differing levels of OK 5415 (Allied Astor Co.) EVA copolymer and $C_{18}$-$C_{22}$ alcohol were added to the wax composition, with no microwax being used.

The ten candles of each set were burn tested for each of the following:

(1) total burn time, in hours, (2) retention of wax after candle has burned, in grams, (3) carbon deposits left on the container after burning, evaluated on a scale of 1 to 5, and (4) coking, evaluated on a scale of 0 to 5 scale.

Burn time is the average amount of time that each candle remained lit, until the candle was completely consumed. Retention refers to the average amount of wax composition that remained after burning the candles to completion. Carbon deposit refers to the average amount of carbon deposit that accumulated on the wicks and was left over after burning the candles. Such deposits are typically found at the bottom of the candle container. This measurement was taken by observing the amount of charred deposit left and rating it on a relative scale. Coking refers to the average amount of carbon deposits found on the side of the containers, and reflects soot that was given off by each candle while it was burning. The coking was also observed and rated.

The Control 1 formula and formulas 1-7 contained the assignee's (S.C. Johnson & Son, Inc.) proprietary scent, Country Garden. The Control 1 formula was manufactured with 5 percent microwax, by weight of the wax composition, with no EVA or HMWA. As can be seen, this candle had the shortest burn time compared to formulas 1-7. Also, this candle had the highest carbon deposits and coking, as well as a relatively high retention of wax residue compared to those other formulas.

Formula 1, containing 2.5 percent EVA, but no A, burned slightly slower and had less retention, as well as marginally less carbon deposits and coking than the control. Formulas 2 and 3 had 5 percent and 12 percent HMWA, respectively, but no EVA. These formulas had lowered retention and reduced carbon deposits and coking. However, with no EVA, such candles would not be preferable because they would be subject to weeping. Formulas 4 and 5 each contained 1 percent EVA and 5 percent HMWA. The HMWA for each was from different sources (one European and the other domestic), assuring that HMWA manufacturing did not significantly affect the results. These candles exhibited longer burn times, less retention, less carbon deposits, and less coking, as compared to Control 1. Formulas 6 and 7 had 3 percent HMWA with 2 and 1 percent EVA, respectively. These candles, while retaining less residual wax, had higher levels of carbon deposit and coking than the compositions used in Formulas 4 and 5.

Although it is apparent from these results that individual candle results may vary, the combination of 1 percent EVA and 5 percent HMWA generally provides for candles with a superior combination of the properties measured than the microwax-containing candles, as well as the candles with either EVA or HMWA alone, demonstrating the effectiveness of the present invention.

Control 2 and Formula 8 each utilize S.C. Johnson & Son, Inc.'s proprietary scent Vanilla, to demonstrate that the invention worked independently of the scent chosen. Control 2, manufactured with 5 percent microwax, did not perform as well as Formula 8, which substituted 1 percent EVA and 5 percent HMWA for the microwax. These results were improved in retention, carbon deposits, coking, and burn time.

We also performed experiments to determine whether the paraffin (main) wax substantially affected the outcome of our invention. These experiments show that the improved qualities provided by the combination of EVA and HMWA in a candle wax composition are achieved independent of the paraffin wax chosen. The results of these experiments are set forth in the table of FIG. 3.

In these experiments, fifteen container candles of each type were also made, with ten being used for evaluation and five being saved as retains. In Controls 3 and 4, 5 percent microwax was used, with no EVA or HMWA.

Each control is compared with two sets of candles that contain the same scent as the control, but 1 percent EVA and 5 percent HMWA, instead of microwax. In addition, for each pair of sets corresponding to a control formula, different paraffins were used. The IGI paraffin wax was obtained from The International Group, Inc. of Agincourt, Ontario, Canada, and the Astor paraffin wax was obtained from The Honeywell-Astor Company of Morristown, N.J.

Control 3, Formula 9 and Formula 10 each utilize S.C. Johnson & Son, Inc.'s proprietary scent Strawberries and Cream. In addition, two different sources of paraffin were utilized in Formulas 9 and 10, as discussed above. The generally similar results for Formulas 9 and 10 confirm that our invention is effective independent of the paraffin chosen, and an improvement over the control formula using a conventional microwax.

Control 4 and formulas 11 and 12 each contain S.C. Johnson & Son, Inc.'s proprietary scent Lavender Meadows. As can be seen in the table in FIG. 3, both formulas 11 and 12 performed slightly better than Control 4, demonstrating the efficacy of our invention. However, we note that improvements on carbon deposits and coking could not be obtained inasmuch as the control itself exhibited neither of these properties. Also, as can be seen, with either choice of paraffin the burn time was improved over Control 4.

Also, each control formula was outperformed by its corresponding experimental formulas further demonstrating the efficacy of our invention among different odorants.

The above examples demonstrate that fragranced candles formed with the compositions according to our invention are generally improved with respect to burn time, retention, carbon deposits and coking, as compared to candles using microwax or other conventional olefinic materials used like microwax to hold fragrance in a candle. Accordingly, our invention provides a fragranced candle wax and candle that is preferable to those products currently available. The examples provided are not intended to be limiting, but are merely demonstrations of the effectiveness of our invention. Other than those exemplified above, many different combinations of components can be used in forming candles according to our invention, while still keeping with the scope of the invention. As discussed above, the choice of components may vary depending on design considerations, and those components may be mixed in various ratios, while still achieving the benefits of our invention. Also, the candle articles may be manufactured by any one of a number of methods.

In other words, while particular embodiments of our invention have been illustrated and described, it will be apparent to those skilled in the art that various changes and modifications may be made without departing from the spirit and scope of our invention. Furthermore, it is intended that the claims will cover all such modifications that are within the scope of our invention.

INDUSTRIAL APPLICABILITY

Our invention is directed to fragranced candle wax compositions and fragranced candle articles that demonstrate improved flame characteristics and lowered smoking and coking, without weeping. We envision our fragranced candle wax compositions and fragranced candle articles will be extremely useful to consumers in any application where there is an interest in imparting fragrance to a space.

We claim:

1. A candle formed of a wax composition, said wax composition comprising:
   (a) a low molecular weight ethylene vinyl acetate, having a molecular weight of at most about 5000 molecular weight units;
   (b) a high molecular weight alcohol, having about 18 to about 22 carbons;
   (c) at least one odorant; and
   (d) a paraffin wax having the formula $C_nH_{2n+2}$, where n is between about 18 and 30, the melting temperature of the paraffin wax is between about 120 and about 160, and the paraffin wax contains 85% or more straight-chain paraffins,
   wherein the combination of said low molecular weight ethylene vinyl acetate, said high molecular weight alcohol, and said wax operate to substantially retain the at least one odorant in said candle when said wax composition is exposed to temperatures below a melting point of said wax composition, and to emit said at least one odorant from said candle when said wax composition is exposed to temperatures at or above the melting point of said wax composition, and
   wherein said composition contains substantially no microwax.

2. A wax composition according to claim 1, wherein the combination of the low molecular weight ethylene vinyl acetate and the high molecular weight alcohol cause the crystalline structure of said wax composition to substantially trap said odorant at temperatures below the melting point.

3. A wax composition as recited in claim 1, wherein said low molecular weight ethylene vinyl acetate is in an amount of about 0.5 percent to about 8 percent by weight.

4. A wax composition as recited in claim 1, wherein said low molecular weight ethylene vinyl acetate is in an amount of about 2 percent to about 5 percent by weight.

5. A wax composition as recited in claim 1, wherein said high molecular weight alcohol is in an amount of about 1 percent to about 20 percent by weight.

6. A wax composition as recited in claim 1, wherein said high molecular weight alcohol is in an amount of about 5 percent to about 15 percent by weight.

7. A wax composition as recited in claim 1, wherein said low molecular weight ethylene vinyl acetate is in an amount of about 0.5 percent to about 8 percent by weight, and said high molecular weight alcohol is in an amount of about 1 percent to about 20 percent by weight.

8. A wax composition as recited in claim 2, wherein said low molecular weight ethylene vinyl acetate is in an amount of about 0.5 percent to about 8 percent by weight, and said high molecular weight alcohol is in an amount of about 1 percent to about 20 percent by weight.

9. A wax composition as recited in claim 1, wherein said low molecular weight ethylene vinyl acetate is in an amount of about 0.5 percent to about 8 percent by weight, and said high molecular weight alcohol is in an amount of about 1 percent to about 20 percent by weight.

10. A wax composition as recited in claim 7, wherein said high molecular weight alcohol is an aliphatic alcohol.

11. A wax composition as recited in claim 7, wherein said at least one odorant is in an amount of about 0.5 percent to about 30 percent by weight.

12. A wax composition as recited in claim 7, further comprising at least one of a pigment and a dye.

13. A wax composition as recited in claim 12, further comprising at least one ultraviolet inhibitor.

14. A wax composition as recited in claim 12, further comprising at least one oxidation inhibitor.

15. A method of making a candle, comprising the steps of:
    (a) heating a wax at least to its melting point;
    (b) mixing (i) a low molecular weight ethylene vinyl acetate, having a molecular weight of at most about 5000 molecular weight units, (ii) a high molecular weight alcohol, having about 18 to about 22 carbons, and (iii) at least one odorant with the wax to form a wax composition;
    (c) casting the wax composition in a mold,
    wherein the combination of the low molecular weight ethylene vinyl acetate, the high molecular weight alcohol, and the wax operate to substantially retain the at least one odorant in the candle when the wax composition is exposed to temperatures below a melting point of the wax composition, and to emit the at least one odorant from the candle when the wax composition is exposed to temperatures at or above the melting point of the wax composition.

16. A method according to claim 15, wherein, in said mixing step, the combination of the low molecular weight ethylene vinyl acetate and high molecular weight alcohol causes crystals of the wax composition cast in said casting step to substantially trap the odorant at or below the melting point.

17. A method according to claim 15, wherein, during said method of making the candle, substantially no microwax is added to the wax composition cast in said casting step.

18. A method according to claim 15, wherein, in said mixing step, the low molecular weight ethylene vinyl acetate is added such that the wax composition comprises about 0.5 percent to about 8 percent by weight of the low molecular weight ethylene vinyl acetate.

19. A method according to claim 15, wherein, in said mixing step, the high molecular weight alcohol is added such that the wax composition comprises about 1 percent to about 20 percent by weight of the high molecular weight alcohol.

20. A method according to claim 19, wherein, in said mixing step, the high molecular weight alcohol is added such that the wax composition comprises about 1 percent to about 20 percent by weight of the high molecular weight alcohol.

21. A method according to claim 19, wherein, in said mixing step, the high molecular weight alcohol added is an aliphatic alcohol.

22. A method according to claim 15, wherein said step of heating the wax composition comprises heating to a temperature lower than about 160 degrees Fahrenheit.

23. A method according to claim 15, wherein, in said mixing step, the high molecular weight alcohol added is an aliphatic alcohol.

24. A candle formed of a wax composition and a wick, said wax composition comprising:
    (a) a low molecular weight ethylene vinyl acetate;
    (b) a high molecular weight alcohol;
    (c) at least one odorant; and
    (d) a wax,
    wherein the combination of said low molecular weight ethylene vinyl acetate, said high molecular weight alcohol, and said wax operate to substantially retain the at least one odorant in said candle when said wax composition is exposed to temperatures below a melting point of said wax composition, and to emit said at least one odorant from said candle when said wax composition is exposed to temperatures at or above the melting point of said wax composition, and
    wherein said composition contains substantially no microwax.

* * * * *